United States Patent [19]

Begley et al.

[11] Patent Number: 5,239,081

[45] Date of Patent: Aug. 24, 1993

[54] PREPARATION OF PHOTOGRAPHIC COMPOUNDS

[75] Inventors: William J. Begley, Webster; Robert C. Stewart, Spencerport, both of N.Y.

[73] Assignee: Eastman Kodak Company, Rochester, N.Y.

[21] Appl. No.: 724,231

[22] Filed: Jul. 1, 1991

[51] Int. Cl.$^5$ .................. C07D 257/04; C07D 265/26; C07C 93/14
[52] U.S. Cl. ..................... 548/251; 544/89; 564/166; 564/99
[58] Field of Search ................. 548/253; 544/89; 564/166, 99

[56] References Cited

U.S. PATENT DOCUMENTS 3,821,254  6/1974  Huyffer et al. ............... 260/343.2
3,869,473  3/1975  Chiang et al. ............... 260/343.2
4,594,426  6/1986  Fujita et al. ............... 548/217
4,840,884  6/1989  Mooberry et al. ............ 430/557

Primary Examiner—David B. Springer
Attorney, Agent, or Firm—Peter C. Cody

[57] ABSTRACT

A process for preparation of a 2,3 or 4-oxo-benzaldehyde or ketone compound by reaction of a 2,3 or 4-hydroxy benzaldehyde or ketone with an ortho, meta or parabromo or chloralkylphenoxy compound comprises reaction of the bromo or chloroalkylphenoxy compound with potassium iodide to form an iodo compound in situ; then, reaction of the resulting product with a 2, 3 or 4-hydroxybenzaldehyde or ketone in the presence of alkylpyridine and a dipolar aprotic solvent. The resulting compounds are useful for formation of photographic color couplers for use in photographic materials.

8 Claims, No Drawings

PREPARATION OF PHOTOGRAPHIC COMPOUNDS

This invention relates to a process for preparation of a 2, 3 or 4-oxo-benzaldehyde or ketone compound by the reaction of a 2, 3 or 4-hydroxybenzaldehyde or ketone with an ortho, meta or parahbromo or chloroalkylphenoxy compound.

It is known in the photographic art that color photographic materials can produce dye images through the selective formation of dyes. It is also known that the dyes can be formed by oxidative coupling. A need has continued for improved processes for preparation of such couplers and related compounds.

One such process that we have investigated has been the preparation of couplers prepared through the reaction of a benzaldehyde compound by reaction of a hydroxybenzaldehyde with a bromoalkyl or chloralkylphenoxy compound, especially such a compound in which the phenoxy compound forms a coupling-off group for a photographic coupler. It was found that reactions that we originally thought would provide an efficient and effective reaction, did not.

It was found that the answer to this problem was a process of preparation of a 2, 3 or 4-oxo-benzaldehye or ketone compound by reaction of a 2, 3, or 4-hydroxybenzaldehyde or ketone with an ortho, meta or parabromo or chloroalkylphenoxy compound; wherein the process comprises reaction of the bromo or chloroalkylphenoxy compound with potassium iodide to form an iodo compound in situ; then, reaction of the resulting product with a 2, 3 or 4-hydroxybenzaldehyde or ketone in the presence of an alkylpyridine, preferably a 2,6-dialkylpyridine, and a dipolar aprotic solvent. Addition of potassium iodide generally increases the rate of the reaction, but the reaction can proceed in its absence.

Such a process enables effective formation of a compound as described that is useful for formation of photographic couplers useful in photographic materials and processes. It was found that the process does not provide effective results for all bases and solvents. For example, the effective results of the described process are not observed when the base is replaced with because they provide low yields or no product.

The bromo or chloroalkylphenoxy compound can be any such compond that reacts with potassium iodide to form the corresponding iodo compound. A preferred bromoalkyl or chloroalkylphenoxy compound is a photographic coupler containing a phenoxy coupling-off group having a bromoalkyl or chloroalkyl group. A preferred bromoalkyl or chloroalkylphenoxy compound is represented by the formula:

COUP - O - Aryl - R$^1$-(Br or Cl)

wherein COUP is a photographic coupler moiety, as known in the photographic art; Aryl is an aryl group, preferably a phenyl group; and -R$^1$-(Br or Cl) is a bromoalkyl or chloroalkyl group, preferably containing 1 to 3 carbon atoms.

An especially useful bromoalkylphenoxy compound is represented by the formula:

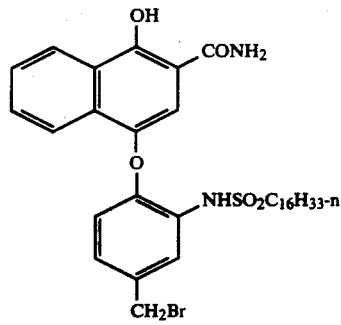

The 2, 3, or 4-hydroxybenzaldahyde or ketone can be any such compound that will react with the described bromoalkyl or chloroalkylphenoxy compound. Such a compound is preferably represented by the formula:

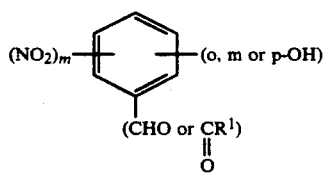

wherein m is 0 or 1; and R$^1$ is alkyl, preferably containing 1 to 3 carbon atoms. The aryl ring can be substituted if desired. A preferred compound within this formula is 4-hydroxy-3-nitrobenzaldehyde.

The 2,6-dialkylpyridine can be any such pyridine compound that contains alkyl groups in the 2- and 6- positions, preferably alkyl containing 1 to 3 carbon atoms, such as methyl or ethyl. An especially preferred compound is 2,6-lutidine.

A dipolar aprotic solvent enables the desired reaction to take place at an effective reaction rate. The terms dipolar and aprotic are used based on the definitions of such terms known in the organic compound art. Preferred solvents are dimethylformamide, dimethylacetamide or acetonitrile, with dimethylacetamide being especially preferred.

The process as described is typically carried out at atmospheric pressure at a temperature within the range of 0 to 100 degrees C., preferably within the range of about 20 to 75 degrees C.

The compounds prepared by the process described are useful for preparing, for example, photographic couplers as described in the following examples.

The following examples further illustrate the invention

EXAMPLE 1

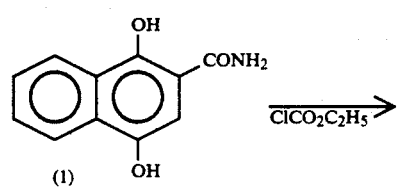

-continued

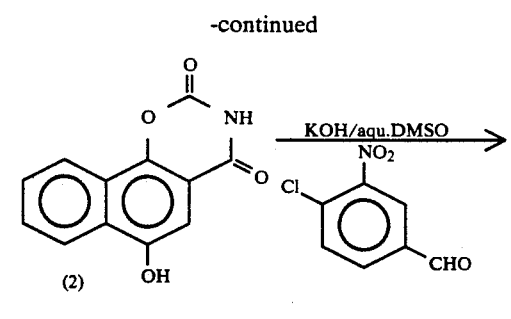
(2)

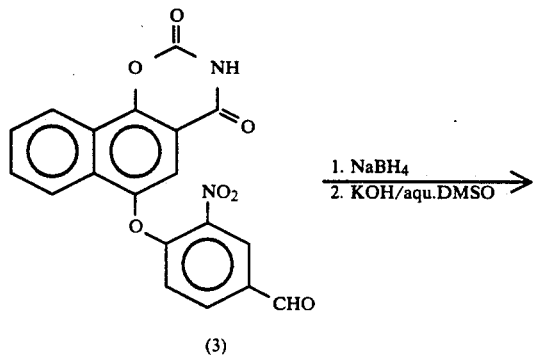
(3)

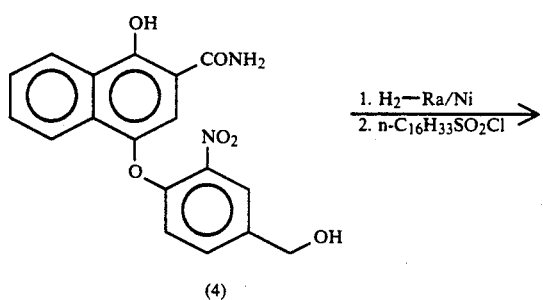
(4)

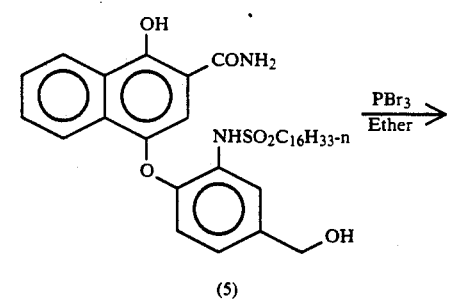
(5)

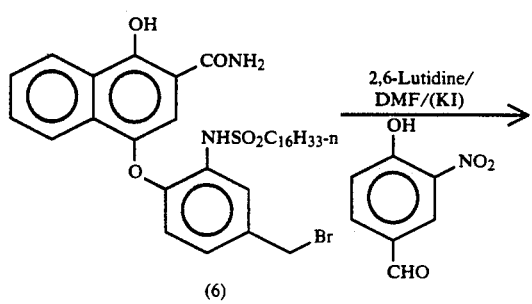
(6)

-continued

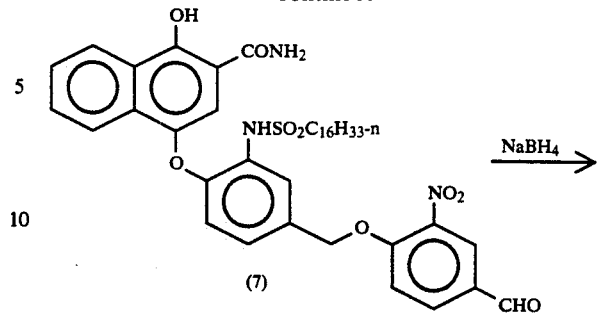
(7)

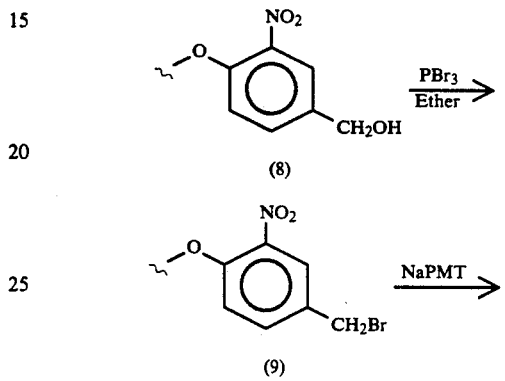
(8)

(9)

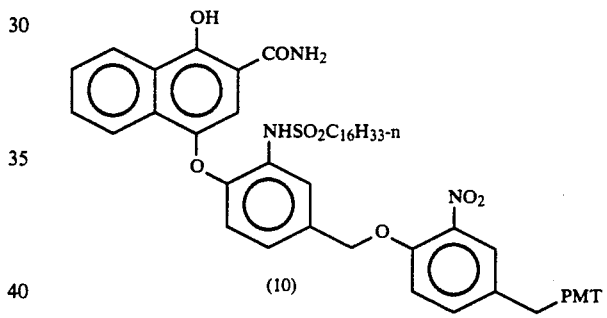
(10)

Compound (1)

Phenyl 1,4-dihydroxy-2-naphthoate (100 g, 356.78 mMole) was dissolved in deoxygenated tetrahydrofuran, (500mL) and deoxygenated methanol, (500mL) added. To this solution, stirred at room temperature under a nitrogen atmosphere, was added ammonium acetate, (50,0 g, 648.63 mMole) followed by concentrated ammonium hydroxide, (1.0 L). After stirring for 3 hours the reaction solution was then poured into ice cold 2N-HCl, (4.0 L) and enough concentrated HCl added to bring the pH to 1. The resulting product, compound (1), was filtered off, washed well with water and air dried. This material was washed with dichloromethane and air dried again. Yield 62.0 g, (72%).

Compound (2)

Compound (1), (50.0 g, 0.246 mMole) was dissolved in dry pyridine, (150 mL) and acetonitrile, (75 mL) added. The solution was stirred and cooled in to $-5°$-$0°$ C. Ethyl chloroformate, (50 mL, 0.523 mMole) was then added dropwise with stirring while maintaining the temperature at 0° C. After the addition, the cooling bath was removed and the temperature allowed to reach room temperature. The reaction mixture was then gradually heated to reflux and the solvent allowed to distill off. This procedure was continued until the temperature had risen to approximately 120° C. and 150 mL of solvent had been collected. Heating under reflux was continued for an additional 1 hour period. The reaction mixture was then cooled to approximately 50° C. and poured into 2N-HCl (3.0 L), held at room temperature. This suspension was then stirred for approximately 15 minutes, filtered and the residue washed well with water, acetonitrile and finally ether. This gave the product, compound (2), sufficiently pure for the next step. Yield 43.5 g, (77%).

Compound (3)

Compound (2), (23.0 g, 100.35 mMole) was taken up in deoxygenated dimethyl sulphoxide, (250 mL) and deoxygenated water, (25 mL) added. To this solution, stirred at room temperature under nitrogen, was added 85% potassium hydroxide, (9.9 g, 150.53 mMole) and stirring continued until dissolution, approximately 15 minutes. 4-Chloro-3-nitrobenzaldehyde, (18.62 g, 100.35 mMole), was then added all at once, and the resulting solution stirred at 60° C. for 1 hour. The reaction mixture was then poured into ice cold 2N-HCl (2.0 L), and filtered off. The product, compound (3), was washed with ether. This product was pure enough to be used in the next step. Yield 28.0 g (74%).

Compound (4)

Compound (3) (28.0 g, 74.01 mMole), in a powdered form, was suspended in tetrahydrofuran, (150 mL) and methanol, (100 mL). Water, (100 mL) was added followed by sodium borohydride, (2.8 g, 74.01 mMole) in small portions. More tetrahydrofuran, (50 mL) was added to aid stirring. At the end of the sodium borohydride addition complete dissolution had been achieved. The reaction was allowed to proceed for a further 15 minutes, then poured into ice cold 2N-HCl (2.0 L), and the product filtered off. The product was washed with methanol and while still wet with solvent, suspended in ethanol and heated to reflux. The solution was cooled, filtered, washed with methanol, ether and finally air dried. A second crop of material was obtained on concentrating the mother liquor. Total yield of the benzyl alcohol precursor to compound (4), 19.5 g, (67%).

The latter compound, (19.0 g, 50 mMole) was suspended in water, (200 mL), containing 85% potassium hydroxide, (26.34 g, 400 mMole). To this mixture was added methanol, (50 mL) and then heated to 80° C. for 1 hour. The resulting dark yellow-brown solution was cooled and poured into ice cold 2N-HCl (2.0 L). The yellow product was filtered off, washed well with water and air dried. Yield of compound (4), 17.7 g (100%).

Compound (5)

Compound (4), 17.7 g, 50 mMole) was dissolved in tetrahydrofuran, (80 mL) and methanol, (300 mL) added. Raney-Nickel which had been washed several times with water an then methanol was added and the solution hydrogenated at 55 psi for 2 hours after which hydrogen uptake had ceased. The catalyst was filtered off, washed with methanol and the filtrate concentrated under reduced pressure to give the product. This product, the amino precursor to compound (5), was deemed sufficiently pure to be carried on to the next step. Yield 100%.

The above amino compound, (50.0 mMole) was dissolved in dry pyridine, (150 mL) and hexadecylsulphonyl chloride, (16.2 g, 50.0 mMole) added. The solution was stirred at room temperature under a nitrogen atmosphere for 30 minutes. The pyridine was concentrated under reduced pressure and the residue taken up in ethyl acetate. This ethyl acetate solution was then washed with 2N-HCl (×3), dried, (MgSO4), filtered and concentrated. The residue which resulted crystallized from acetonitrile. After filtering, washing with acetonitrile and drying, the yield of product, compound (5), amounted to 16.3 g, {53% calculated from compound (4)}.

Compound (6)

Compound (5), (4.0 g, 6.53 mMole) was suspended in dry ether, (30 mL) and phosphorous tribromide, (0.68 mL, 7.18 mMole) in ether, (20 mL) added dropwise over a 15 minute period. After the addition the reaction was diluted with ether and the ether solution washed with 2N-HCl (×1), dried, (MgSO4), filtered and concentrated to give compound (6). The yield was 100%.

Compound (7)

Compound (6), (13.5 g, 19.98 mMole) was dissolved in DMF, (100 mL), and 4-hydroxy-3-nitrobenzeldehyde, (3.34 g, 19.98 mMole) followed by 2,6-butidine, (4.6 mL, 40 mMole) were added. The reaction solution was stirred at room temperature for 24 hours. A further batch of base, (4.64 mL), was added and the reaction solution stirred for a further 24 hours. After this period the temperature of the reaction was raised to 60° C. and held there with stirring for a further 24 hours. At the end of this period the reaction was worked up by dilution with ethyl acetate and washing the ethyl acetate layer with 2N-HCl (×2), 2%-Na2CO3 (×3). 2N-HCl (×1), dried (MgSO4), filtered and concentrated under reduced pressure to an oil. This oil was dissolved in a solvent mixture of ethyl acetate (20), dichloromethane (5) and heptane (30), and pressure chromatographed over silica gel eluting with the same solvent mixture. Three major components were collected in the following order of increasing polarity; the formulated derivative of compound (5), the product compound (7), and the benzyl alcohol compound (5). The yield of compound (7) was 3.4 g, (22%)

Compound (8)

Compound (7), (9.5 g, 12.47 mMole) was dissolved in THF (30 mL), and methyl alcohol (30 mL) added. Sodium borohydride (0.47 g, 12.47 mMole) was gradually added while stirring. After the sodium brohydride had been added the resulting solution was stirred at room temperature for 15 minutes. The reaction solution was then concentrated, taken up in ethyl acetate and the ethyl acetate solution washed with 2N-HCl (×1), dried (MgSO4), filtered and concentrated to an oil under reduced pressure. This oil, compound (8), was used directly in the next step but can be crystallized pure form ether.

Compound (9)

Compound (8), (12.47 mMole), was dissolved in a 50% solution of THF and ether (100 mL). Phosphorus tribromide (1.2 mL, 12.47 mMole) in ether (20 mL) was then added dropwise. At the end of the addition the reaction solution was stirred at room temperature for 15 minutes. The reaction was then diluted with ethyl acetate, washed with 2N-HCl (×1), brine (×1), dried (MgSO4), filtered and concentrated to an oil. This oil, compound (9), was used directly in the next step of the sequence.

Compound (10)

Compound (9), (12,47 mMole) was dissolved in DMF (60 mL) and NaPMT, (2.5 g, 12.47 mMole) added. The reaction was stirred at room temperature for 15 minutes. It was then diluted with ethyl acetate, washed with 2N-HCl (×1), 2.5%-Na₂CO₃ (×1), 2N-HCl (×1), brine (×1), dried (MgSO₄), filtered and concentrated under reduced pressure to an oil. This oil was dissolved in a solvent mixture of ethyl acetate (15), dichloromethane (5), and heptane (30) and pressure chromotographed over silica gel eluting with the same solvent mixture. Yield of compound (10), 9.8 g (85%). Calculated for $C_{48}H_{57}O_8S_2$: % C 62.38, % H 6.22, % N 10.61, % S 6.14. Found: % C 62.15, % H 6.23, % N 10.19, % S 7.21.

The invention has been described in detail with particular reference to preferred embodiments thereof, but it will be understood that variations and modifications can be effected within the spirit and scope of the invention.

What is claimed is:

1. In a process of making a photographic coupler which forms a wash-out dye and releasing a PUG which is essentially a 2,3 or 4-oxo-benzaldehyde or ketone compound, the compound being formed by reaction of a 2, 3, or 4-hydroxybenzaldehyde or ketone with an ortho, meta or para bromo or chloroalkylphenoxy compound; comprising reaction of the bromo or chloroalkylphenoxy compound, optionally with potassium iodide to form an iodo compound in situ, then reaction of the resulting product with a 2, 3 or 4-hydroxybenzaldehyde or ketone wherein the improvement is reaction of the latter in the presence of 2,6-dialkylpyridine and a dipolar aprotic solvent.

2. A process as in claim 1 wherein the bromoalkylphenoxy compound is

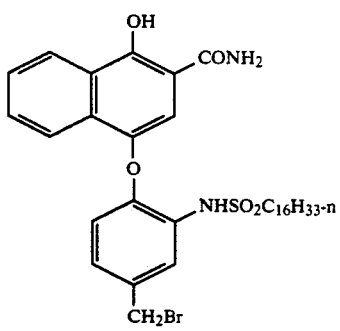

3. A process as in claim 1 wherein the 2, 3 or 4-hydroxybenzaldehyde or ketone is 4-hydroxy-3-nitrobenzaldehyde.

4. A process as in claim 1 wherein the 2,6-dialkylpyridine is 2,6-lutidine.

5. A process as in claim 1 wherein the dipolar aprotic solvent is dimethylacetamide or dimethylformamide.

6. A process as in claim 1 comprising reacting a compound of the formula

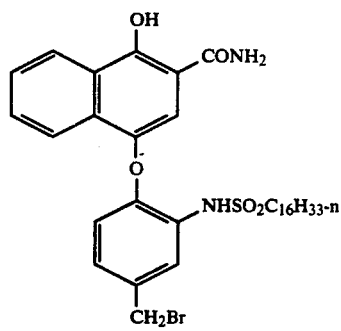

with potassium iodide to form the corresponding iodo compound in situ; then reacting the resulting product with

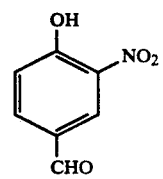

in the presence of 2,6-lutidine in dimethylacetamide to form a compound of the formula:

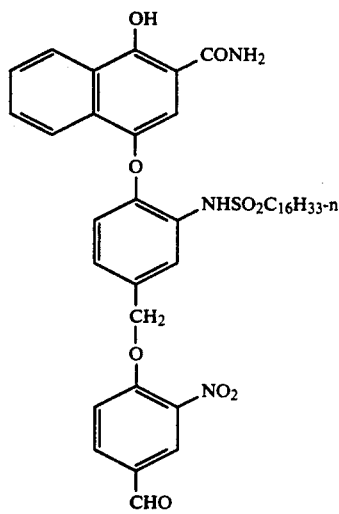

7. A process of forming a compound of the formula:

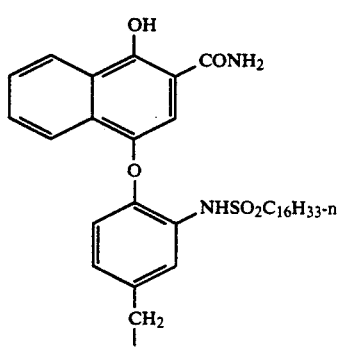

-continued

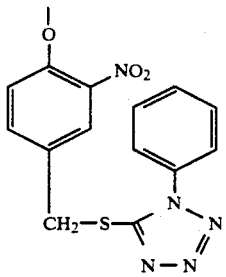

comprising reacting a compound of the formula:

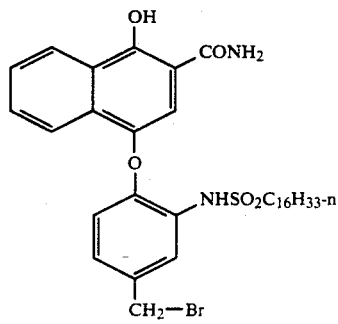

with potassium iodide to form the corresponding iodo compound in situ; then reacting the resulting product with

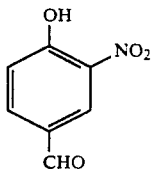

in the presence of 2,6-lutidine in dimethylacetamide; then reacting the resulting aldehyde product with NaBH$_4$ to form the corresponding —CH$_2$OH compound; then reacting the resulting —CH$_2$OH compound with PBr$_3$ in ether to form the corresponding —CH$_2$Br compound; and, then reacting the resulting —CH$_2$Br compound with sodium phenylmercaptotetrazole, followed by isolation of the product compound.

8. In a process for preparation of a 2, 3 or 4-oxo-benzaldehyde or ketone compound by reaction of a 2, 3, or 4-hydroxybenzaldehyde or ketone represented by the formula:

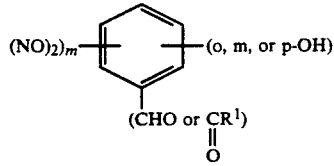

wherein
m is 0 or 1; and
R$^1$ is alkyl containing 1 to 3 carbon atoms; with an ortho, meta or para bromo or chloroalkyphenoxy compound represented by the formula

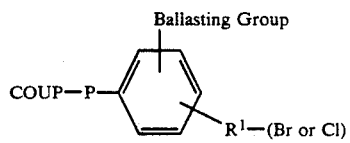

wherein
COUP is a photographic coupler moiety; R$^1$-(Br or Cl) is a bromoalkyl or chloroalkyl group containing 1 to 3 carbon atoms, and Ballasting Group is a photographic ballast group which is not reactive under the conditions employed herein, wherein the process optionally includes the reaction of the bromo or chloroalkylphenoxy compound with potassium iodide to form an iodo compound in situ; then reaction of the bromo or chloroalkyphenoxy compound with a 2, 3 or 4-hydroxybenzaldehyde or ketone, wherein the improvement is carrying out this latter reaction in the presence of a 2,6-dialkylpyridine and a dipolar aprotic solvent.

* * * * *

UNITED STATES PATENT AND TRADEMARK OFFICE
CERTIFICATE OF CORRECTION

PATENT NO. : 5,239,081
DATED : August 24, 1993
INVENTOR(S) W. J. Begley, et. al.

It is certified that error appears in the above-indentified patent and that said Letters Patent is hereby corrected as shown below:

Column 10, second structure, delete "COUP-P" and insert --COUP-O--.

Signed and Sealed this

Fifth Day of April, 1994

Attest:

BRUCE LEHMAN

*Attesting Officer*  *Commissioner of Patents and Trademarks*